(12) United States Patent
Magara (10) Patent No.: US 12,109,331 B2
(45) Date of Patent: Oct. 8, 2024

(54) MEDICAL DEVICE, AND METHOD FOR MANUFACTURING MEDICAL DEVICE

(71) Applicant: OLYMPUS CORPORATION, Hachioji (JP)

(72) Inventor: Takashi Magara, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 17/467,637

(22) Filed: Sep. 7, 2021

(65) Prior Publication Data

US 2021/0402067 A1 Dec. 30, 2021

Related U.S. Application Data

(63) Continuation of application No. PCT/JP2020/008921, filed on Mar. 3, 2020.

(30) Foreign Application Priority Data

Mar. 8, 2019 (JP) .................................. 2019-042807

(51) Int. Cl.
*A61L 29/04* (2006.01)
*A61B 1/005* (2006.01)
(Continued)

(52) U.S. Cl.
CPC .............. *A61L 29/16* (2013.01); *A61B 1/005* (2013.01); *A61L 29/049* (2013.01);
(Continued)

(58) Field of Classification Search
CPC ..... A61B 1/00; A61B 1/005; A61L 2300/404; A61L 2420/02; A61L 29/041;
(Continued)

(56) References Cited

U.S. PATENT DOCUMENTS

2007/0156115 A1\* 7/2007 Hosoi .................. A61B 1/0055
604/525
2008/0114205 A1 5/2008 Kagawa et al.
(Continued)

FOREIGN PATENT DOCUMENTS

CN 106061733 A 10/2016
JP 2002308965 A 10/2002
(Continued)

OTHER PUBLICATIONS

International Search Report (ISR) (and English language translation thereof) dated Jun. 2, 2020 issued in International Application No. PCT/JP2020/008921.

(Continued)

*Primary Examiner* — Yan Lan
(74) *Attorney, Agent, or Firm* — Holtz, Holtz & Volek PC (57) ABSTRACT

A medical device includes a resin base including one or more than one material selected from a group consisted by an ethylene propylene resin containing fluorine, a styrene resin containing fluorine, an olefin resin containing fluorine, a vinyl chloride resin containing fluorine, a polyester resin containing fluorine, a polyurethane resin containing fluorine, and a nylon resin containing fluorine; an underlayer formed on the resin base, the underlayer including an oxazolidone ring; and an epoxy resin layer formed on the underlayer.

9 Claims, 4 Drawing Sheets

(51) Int. Cl.
*A61L 29/16* (2006.01)
*C08L 27/18* (2006.01)
*C08L 27/20* (2006.01)
*C08L 63/00* (2006.01)

(52) U.S. Cl.
CPC ........... *A61L 2420/02* (2013.01); *C08L 27/18* (2013.01); *C08L 27/20* (2013.01); *C08L 63/00* (2013.01)

(58) Field of Classification Search
CPC ...... A61L 29/049; A61L 29/16; A61L 31/048; A61L 31/16; B05D 1/36; B32B 27/30; B32B 27/38; C08L 27/18; C08L 27/20; C08L 63/00; C09D 163/00; C09D 201/02; C09D 5/00
See application file for complete search history.

(56) References Cited

U.S. PATENT DOCUMENTS

| | | |
|---|---|---|
| 2010/0279109 A1 | 11/2010 | Ootake et al. |
| 2011/0108094 A1 | 5/2011 | Nishijima et al. |
| 2011/0237050 A1* | 9/2011 | Sugimura ............... H01L 21/78 257/E21.599 |

FOREIGN PATENT DOCUMENTS

| | | |
|---|---|---|
| JP | 2006218102 A | 8/2006 |
| JP | 2007151693 A | 6/2007 |
| JP | 2010278427 A | 12/2010 |
| JP | 2011204806 A | 10/2011 |
| WO | 2009157545 A1 | 12/2009 |

OTHER PUBLICATIONS

Chinese Office Action (and an English language translation thereof) dated Apr. 30, 2024, issued in counterpart Chinese Application No. 202080010940.2.

* cited by examiner

MEDICAL DEVICE, AND METHOD FOR MANUFACTURING MEDICAL DEVICE

The present application is a continuation application of PCT International Application No. PCT/JP2020/008921, filed on Mar. 3, 2020, whose priority is claimed on Japanese Patent Application No. 2019-042807, filed on Mar. 8, 2019. The contents of the PCT International Application and the Japanese Patent Application are incorporated herein by reference.

TECHNICAL FIELD

The present disclosure relates to a medical device and a method for manufacturing a medical device.

BACKGROUND ART

Various drugs may be used for disinfection and sterilization of medical devices such as an endoscope and the like. The drugs act on the bacteria as well as on the components of the medical devices. There are cases where the drugs may deteriorate the materials of the components of the medical devices.

For example, in Japanese Unexamined Patent Application, First Publication No. 2006-218102, the technology of dispersing the acrylic rubber fine particles in an epoxy adhesive so as to suppress peeling of the epoxy adhesive after the disinfection and the sterilization is proposed.

According to the technology disclosed in Japanese Unexamined Patent Application, First Publication No. 2006-218102, the acrylic rubber is blended with a bisphenol-based epoxy resin to denature the bisphenol-based epoxy resin for the purpose of improving the adhesive shear strength and the adhesive peel strength. As a result, the adhesive shear strength and the adhesive peel strength between the metal members and the rubber members are improved.

However, there are cases in which the fluorine-based material may be exposed on the outer surface of part of the configuration members of the medical device. Since the fluorine-based material is a material difficult to adhere, even the technology disclosed in Japanese Unexamined Patent Application, First Publication No. 2006-21.8102 is adopted, the adhesion between the adherend body and the adhesive is low. As a result, when at least one of the adherend bodies is formed from the fluorine-based material, there are cases where the adhesive may float or peel off due to the attack by the chemical solution for disinfection or sterilization.

SUMMARY

According to a first aspect of the present disclosure, a medical device includes a resin base including one or more than one material selected from a group consisted by an ethylene propylene resin containing fluorine, a styrene resin containing fluorine, an olefin resin containing fluorine, a vinyl chloride resin containing fluorine, a polyester resin containing fluorine, a polyurethane resin containing fluorine, and a nylon resin containing fluorine; an underlayer formed on the resin base, the underlayer including an oxazolidone ring; and an epoxy resin layer formed on the underlayer.

According to a second aspect of the present disclosure, in the medical device according to the first aspect, a composite layer including the material of the resin base may be formed at least in a lower portion of the underlayer.

According to third aspect of the present disclosure, in the medical device according to the second aspect, the thickness of the composite layer may be equal to or more than 2 nanometers and equal to or less than 800 nanometers.

According to a fourth aspect of the present disclosure, in the medical device according to the first aspect, the underlayer may further include a substance having an unsaturated bond of carbon atoms.

According to a fifth aspect of the present disclosure, in the medical device according to the first aspect, resin base may further include a substance having an unsaturated bond of carbon atoms.

According to a sixth aspect of the present disclosure, a method for manufacturing a medical device includes a step of preparing a resin base including one or more than one material selected from a group consisted by an ethylene propylene resin containing fluorine, a styrene resin containing fluorine, an olefin resin containing fluorine, a vinyl chloride resin containing fluorine, a polyester resin containing fluorine, a polyurethane resin containing fluorine, and a nylon resin containing fluorine; a step of preparing a solution in which isocyanate is mixed in an organic solvent; a step of adhering the solution on a surface of the rein base material and drying the solution to form an underlayer; and a step of coating an epoxy resin raw material on the underlayer and curing the epoxy resin raw material to form an epoxy resin layer.

According to a seventh aspect of the present disclosure, the method for manufacturing a medical device according to the sixth aspect may further includes a step of forming a composite layer in a lower portion of the underlayer, wherein the material of the underlayer and the material of the resin base are mixed in the composite layer.

DESCRIPTION OF EMBODIMENTS

Hereinafter, a medical device and a method for manufacturing the medical device according to an embodiment of the present disclosure will be described with reference to the accompanying figures. In all of the figures, the same or corresponding members are designated with the same reference numerals, and a common description will be omitted.

Figure 1:
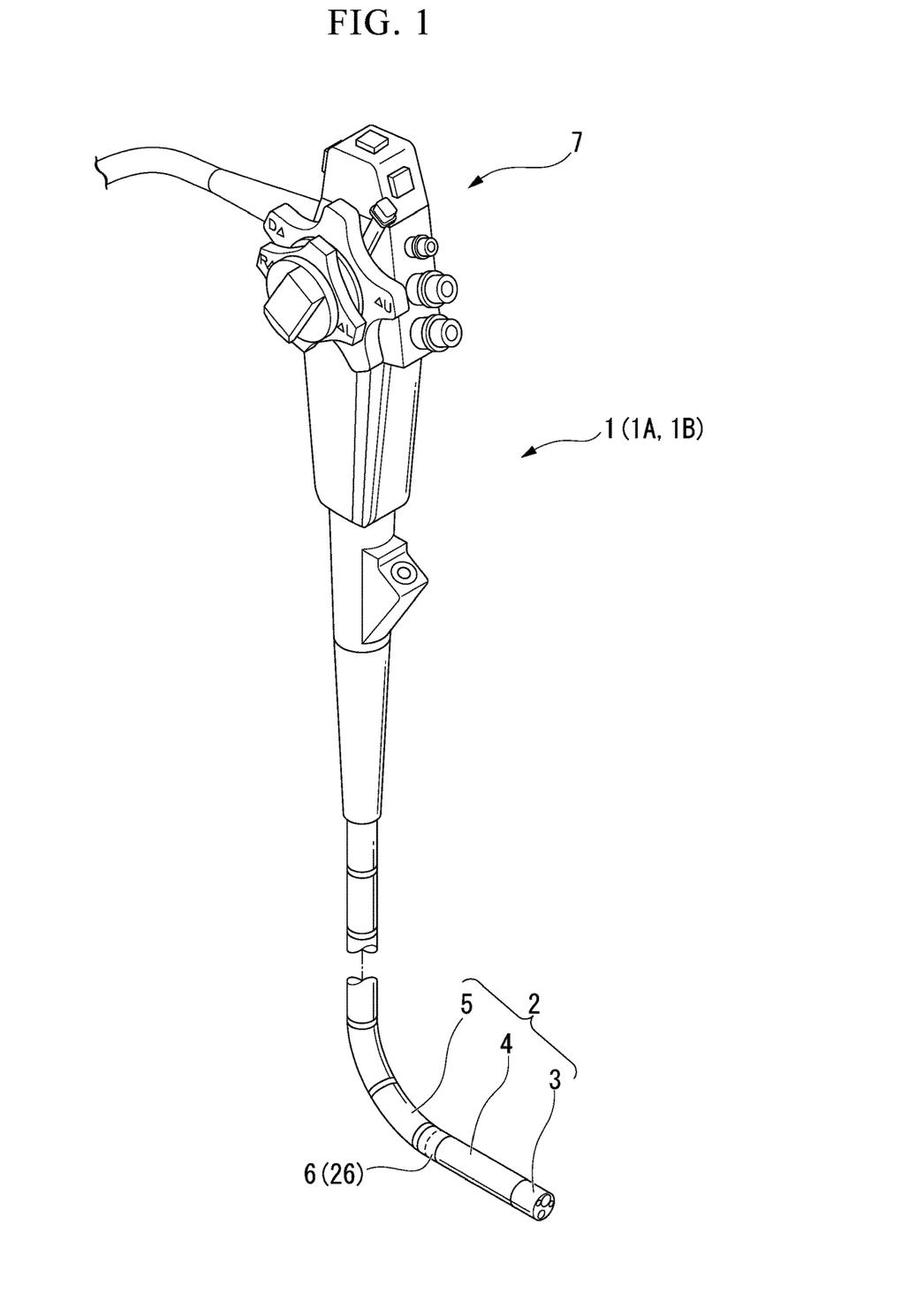
FIG. 1 is a perspective view schematically showing a configuration example of a medical device according to an embodiment of the present disclosure.
Figure 2:
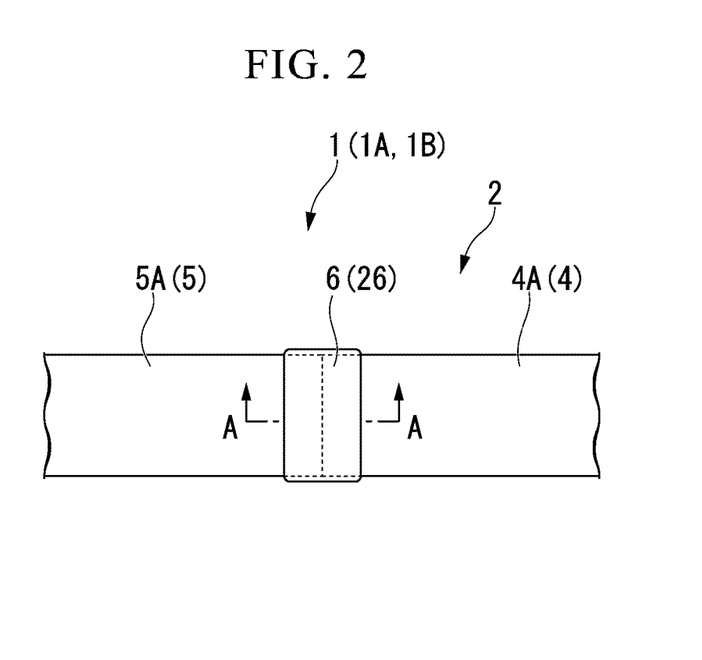
FIG. 2 is a planar view schematically showing an adhesion portion of the medical device.

FIG. 1 is a schematic perspective view showing a configuration example of a medical device according to an embodiment of the present disclosure. FIG. 2 is a schematic planar view showing an adhesion portion in the medical device.

As shown in FIG. 1, an endoscope 1 (medical device) according to the present embodiment includes an insertion portion 2 and an operation portion 7.

The insertion portion 2 is configured to be inserted into the body of a patient. The insertion portion 2 is formed to be tubular. The insertion portion 2 has flexibility. The insertion portion 2 has a distal end portion 3, a bending portion 4, and a flexible tube portion 5 in this sequence from the distal end side along an insertion direction. Inside the insertion portion 2, a treatment device channel for inserting a treatment device may be provided in a longitudinal direction of the insertion portion 2.

The distal end portion 3 is arranged at the most distal end portion of the endoscope 1. The distal end portion 3 has a columnar shape. The distal end portion 3 includes an imaging sensor and an imaging optical system inside. An imaging window and an illumination window are formed at the distal end of the distal end portion 3. In a case in which the insertion portion 2 includes the treatment device channel, an opening of the treatment device channel is provided at the distal end of the distal end portion 3.

The bending portion 4 is connected to the proximal end side of the distal end portion 3. The bending portion 4 is configured to change the orientation of the distal end portion 3. The bending portion 4 is a tubular portion that can be bent.

The bending portion 4 includes, for example, a plurality of nodal rings. Each of the plurality of nodal rings has a circular shape. Each of the plurality of nodal rings is connected to the adjacent nodal ring to be rotatable. In the bending portion 4, a plurality of angle wires are inserted through the plurality of nodal rings.

For example, a member such as an electric wiring, a light guide or the like is accommodated in the bending portion 4. The electrical wiring is connected to the imaging sensor provided at the distal end portion 3. The light guide is formed to extend to the illumination window.

The members such as the electrical wiring and the light guide are inserted through the flexible tube portion 5 described below. The members such as the electrical wiring and the light guide extend to the operation portion 7 described below.

As shown in FIG. 2, an external skin 4A (resin base) is provided on the most outside portion of the bending portion 4.

The external skin 4A is a tube that covers the outer circumference of a plurality of nodal rings. The external skin 4A is formed from a flexible resin material. According to the present embodiment, the resin material of the external skin 4A contains fluorine for the purpose of improving the slidability with respect to the living tissue and the like.

The resin material forming the external skin 4A may be a resin selected from a group consisted by an ethylene propylene resin containing fluorine, a styrene resin containing fluorine, an olefin resin containing fluorine, a vinyl chloride resin containing fluorine, a polyester resin containing fluorine, a polyurethane resin containing fluorine, and a nylon resin containing fluorine.

The "resin containing fluorine" means that fluorine atoms are contained in part of the compound included in the resin.

For example, the fluorine atoms may be arranged on the side chain of the resin polymer or at the end of the resin polymer. For example, the fluorine atoms may be arranged in part of the compound added to the resin material. For example, when the external skin 4A is formed from a composite of a plurality of resin materials, at least one resin material among the plurality of resin materials may contain the fluorine atoms.

Since the fluorine group is exposed on at least part of the surface of the "resin containing fluorine", the slidability on the surface becomes superior. On the other hand, on the surface of the "fluorine-containing resin", the hydrophobicity due to the fluorine group becomes high such that the adhesiveness with respect to the adhesive is decreased.

It is more preferable that the resin material used for the external skin 4A further contains a substance having an unsaturated bond between carbon atoms. The type of the substance having the unsaturated bond between carbon atoms is not particularly limited. For example, an acrylic resin containing fluorine, a vinyl ester resin containing fluorine, a vinyl acetate resin containing fluorine, and a vinylidene resin containing fluorine are taken as examples of the substance having an unsaturated bond between carbon atoms.

As shown in FIG. 1, the flexible tube portion 5 is a tubular portion that connects the bending portion 4 and the operation portion 7 described later.

The flexible tube portion 5 includes, for example, a corrugated tube (not shown) and an external skin 5A (see resin base in FIG. 2). The corrugated tube is a member formed by winding a metal or resin strip-shaped member.

As shown in FIG. 2, the external skin 5A is arranged on the outermost side of the flexible tube portion 5. The external skin 5A is a tube configured to cover the outer circumference of the corrugated tube. An end portion of the external skin 5A being opposite to the bending portion 4 is opposite to an end portion of the external skin 4A of the bending portion 4.

An outer diameter of the external skin 5A may be the same as the outer diameter of the external skin 4A or different from the outer diameter of the external skin 4A. In the example shown in FIG. 2, the outer diameter of the external skin 5A and the outer diameter of the external skin 4A are equal to each other.

The external skin 5A is made of a flexible resin material. According to the present embodiment, the resin material of the external skin 5A contains fluorine for the purpose of improving the slidability with respect to the living tissue or the like.

Similar to the external skin 4A, the resin material containing fluorine is used as the resin material for forming the external skin 5A. All of the resin materials that may be used as the external skin 4A can also be used as the resin material of the external skin 5A. The resin material forming the external skin 5A may be the same resin material as that of the external skin 4A, or different from that of the external skin 4A.

Although it is not particularly shown in figures, two systems of angle wires including at least a first angle wire and a second angle wire are arranged inside the flexible tube portion 5. Each angle wire is inserted through a coil sheath. Each angle wire is arranged to extend from the bending portion 4 toward the proximal end side.

Similar to the bending portion 4, the members such as the above-described electrical wiring and the light guide are inserted through the flexible tube portion 5.

In the example shown in FIG. 2, the end portion of the external skin 4A and the end portion of the external skin 5A being opposite to each other are joined by an adhesion portion 6 in a state in which the end portion of the external skin 4A and the end portion of the external skin 5A are in contact with each other in the axial direction.

The adhesion portion 6 covers the entire circumference of the external circumferential portion of the end portion of the external skin 4A, the external circumferential portion of the end portion of the external skin 5A, and the contact portion of the external skin 4A and the external skin 5A.

However, the external skin 4A and the external skin 5A may be separated to be apart in the axial direction. In this case, the adhesion portion 6 is filled in a gap between the external skin 4A and the external 5A with.

The detailed configuration of the adhesion portion 6 will be described below.

As shown in FIG. 1, the operation portion 7 is a device portion with which the operator operates the endoscope 1. As operations performed via the operation portion 7, an operation of pulling the angle wire for the purpose of changing a bending amount of the bending unit 4 is taken as an example. The operation portion 7 includes an operation portion main body grasped by the operator and various operation members provided on the operation portion main body. For example, the various operation members may be an operation knob, an operation switch, and the like.

Next, the detailed configuration of the adhesion portion 6 will be described.

Figure 3:
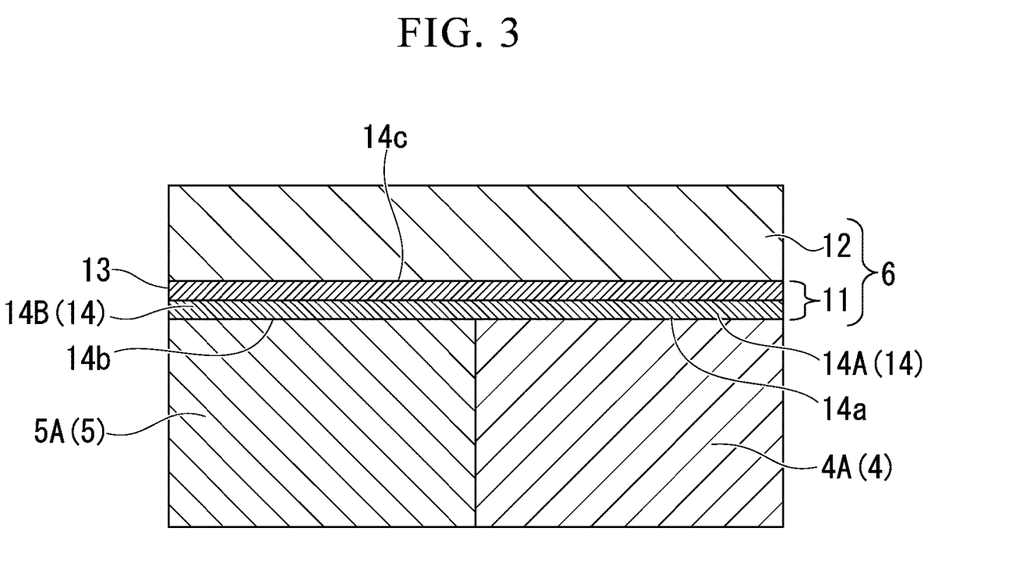
FIG. 3 is a cross-sectional view along the line A-A in FIG. 2.

FIG. 3 is a cross-sectional view taken along the line A-A in FIG. 2. However, since FIG. 3 is an enlarged view, the configurations at the internal side of the external skin 4A and the external skin in the thickness direction are not shown.

As shown in FIG. 3, the adhesion portion 6 includes an underlayer 11 and an epoxy resin layer 12.

The underlayer 11 is formed from an underlayer main body 13 bonded to the epoxy resin layer 12 and a composite layer 14 formed on the surfaces of the external skin 4A and external skin 5A.

The underlayer body 13 is formed from a substance containing at least an oxazolidone ring formed between the underlayer body 13 and the epoxy resin layer 12. The raw material of the underlayer main body 13 is the isocyanate. The reason why the substance containing the oxazolidene ring is contained in the underlayer body 13 is that the oxazolidene ring is generated during the chemical reaction between the isocyanate and the epoxy resin layer 12 in the manufacturing process described below.

However, the underlayer main body 13 may contain a polymer other than the epoxy resin contained in the epoxy resin layer 12, a substance generated by the isocyanate reacting with water or the like, the unreacted isocyanate, or the like.

The composite layer 14 is formed from a first composite layer 14A formed between the external skin 4A and the underlayer main body 13, and a second composite layer 14B formed between the external skin 5A and the underlayer main body 13. However, in the vicinity of the contact portions of the external skin 4A and external skin 5A, the first composite layer 14A and the second composite layer 14B are mixed without forming a clear boundary such that in FIG. 3, the boundary line is not shown.

The first composite layer 14A is a layered portion formed by combining the material of the external skin 4A (referred to as a first base material) and the material of the underlayer main body 13 (referred to as an underlayer material). The first composite layer 14A is formed between an upper boundary surface 14c where the first base material starts to be mixed with the underlayer material and a lower boundary surface 14a where the underlayer material is not mixed with the first base material.

For example, in the first composite layer 14A, the first base material and the underlayer material may be mixed with each other in a state where the boundary is not clear as a whole.

For example, in the first composite layer 14A, the first base material and the underlayer material may be composited in a state where a clear interface is formed or a boundary portion where the first base material and the base material are mixed with each other is formed. However, in a case in which the interface or the boundary portion is formed, the interface or the boundary portion is formed to have a concave-convex shape the layer thickness direction. In this case, when a cross section of the first composite layer 14A intersecting the layer thickness direction is taken, the composite layer is formed to have the cross section in which the first base material and the underlayer material are distributed in a mottled pattern.

A composition ratio of the first base material and the underlayer material in the layer thickness direction is not particularly limited. However, for the purpose of further strengthening the bond force of the first composite layer 14A with the epoxy resin layer 12 and the external skin 4A, it is more preferable that the composition ratio of the first base material increases as it approaches the upper boundary surface 14c, and it is more preferable that the composition ratio of the underlayer material increases as it approaches the lower boundary surface 14a.

The second composite layer 14B is a layered portion formed by combining the material of the external skin 5A (referred to as a second base material) and the underlayer material. The second composite layer 14B is formed between the upper boundary surface 14c and the lower boundary surface 14b where the underlayer material is not mixed with the second base material.

The second composite layer 14B is formed in the same manner as that of the first composite layer 14A, except that the first base material and the external skin 4A are replaced with the second base material and the external skin 5A, respectively.

The thickness of the underlayer main body 13 may exceed zero nm and equal to or less than 100 nm. The thickness of the underlayer main body 13 is more preferably to be equal to or more than 20 nm and equal to or less than 70 nm.

When the thickness of the underlayer main body 13 is zero nm, the epoxy resin layer 12 comes into contact with part of the first base material and the second base material contained in the composite layer 14 such that the adhesive strength with the epoxy resin layer 12 may decrease due to the fluorine groups contained in first base material and the second base material.

If the thickness of the underlayer main body 13 exceeds 100 nm, an internal stress of the underlayer 11 increases such that the adhesion strength with the external skin 4A and the external 5A may decrease.

The thickness of the composite layer 14 may be equal to or more than 2 nm and equal to or less than 800 nm. The thickness of the composite layer 14 is more preferably to be equal to or more than 10 nm and equal to or less than 300 nm.

If the thickness of the composite layer 14 is less than 2 nm, the bonding force between the external skin 4A, the external skin 5A and the underlayer 11 may become too low.

If the thickness of the composite layer 14 exceeds 800 nm, the internal stress of the composite layer 14 increases such that the adhesion strength with the epoxy resin layer 12 may decrease.

It is more preferable that the underlayer 11 further contains a substance having an unsaturated bond between carbon atoms. The 2-isocyanatoethylacryllate and the 2-isocyanatoethyl methacrylate may be taken as the examples of substances having an unsaturated bond between carbon atoms.

The epoxy resin layer 12 is formed on the underlayer main body 13 of the underlayer 11. The epoxy resin layer 12 is formed on the underlayer main body 13 over the entire circumference in the circumferential direction.

The material of the epoxy resin layer 12 is formed by curing a mixture of an epoxy resin and a curing agent (epoxy resin raw material) as a raw material.

The epoxy resin only has to be a resin material having an epoxy group, and the epoxy resin itself is not particularly limited. For example, as the epoxy resin, a resin denatured by a silicone functional group, a urethane functional group, or an acrylic functional group may be used. A bisphenol A type epoxy resin, a novolac type epoxy resin, a cyclic aliphatic type epoxy resin, a glycidyl ester type epoxy resin, a hydride in type epoxy resin, an isocyanurate type epoxy resin and the like are taken as specific examples of the epoxy resin.

The type of curing agent for curing the epoxy resin may be selected in accordance with the type of the epoxy resin. For example, an aromatic amine-based curing agent, an aliphatic amine-based curing agent, an acid anhydride-based curing agent, and a polyamide-based curing agent are taken as examples of the curing agent.

Various additives such as an antioxidant, a metal inactivating agent, and an ultraviolet absorber may be added to the epoxy resin layer 12.

A method for manufacturing the endoscope 1 will be described focusing on the manufacturing method of the adhesion portion 6.

Figure 4A:
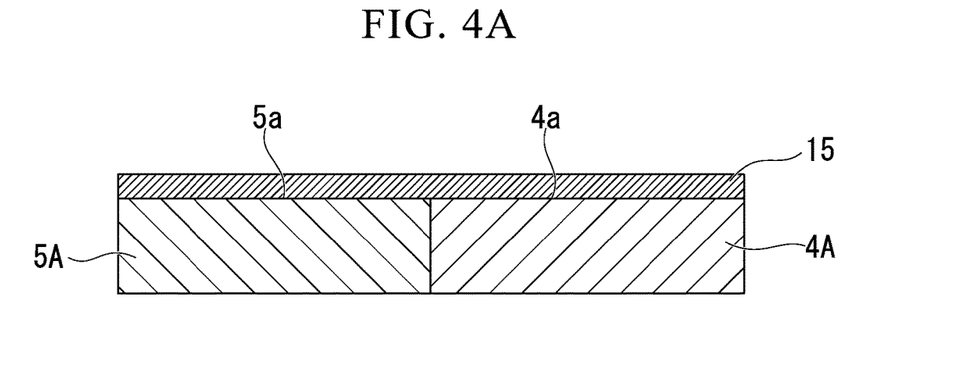
FIG. 4A is a process chart schematically showing a method for manufacturing a medical device according to an embodiment of the present disclosure.
Figure 4B:
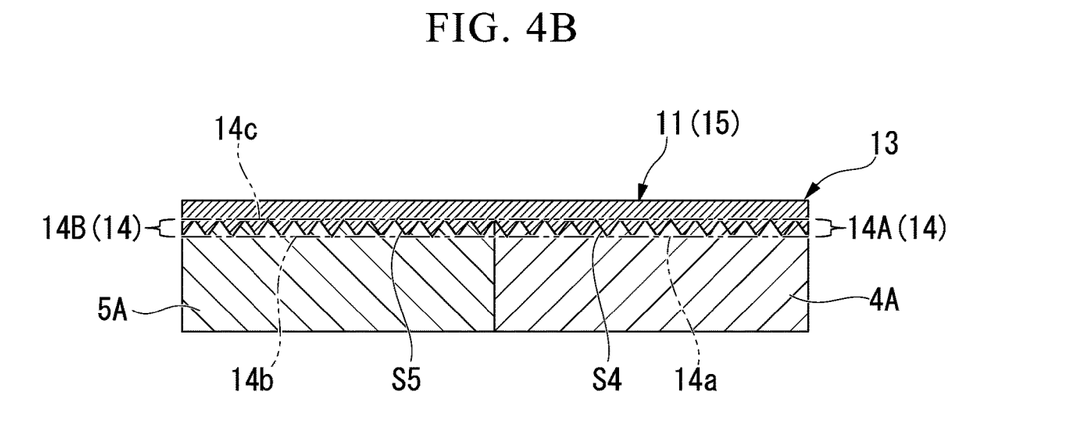
FIG. 4B is a process chart schematically showing the method for manufacturing a medical device.
Figure 4C:
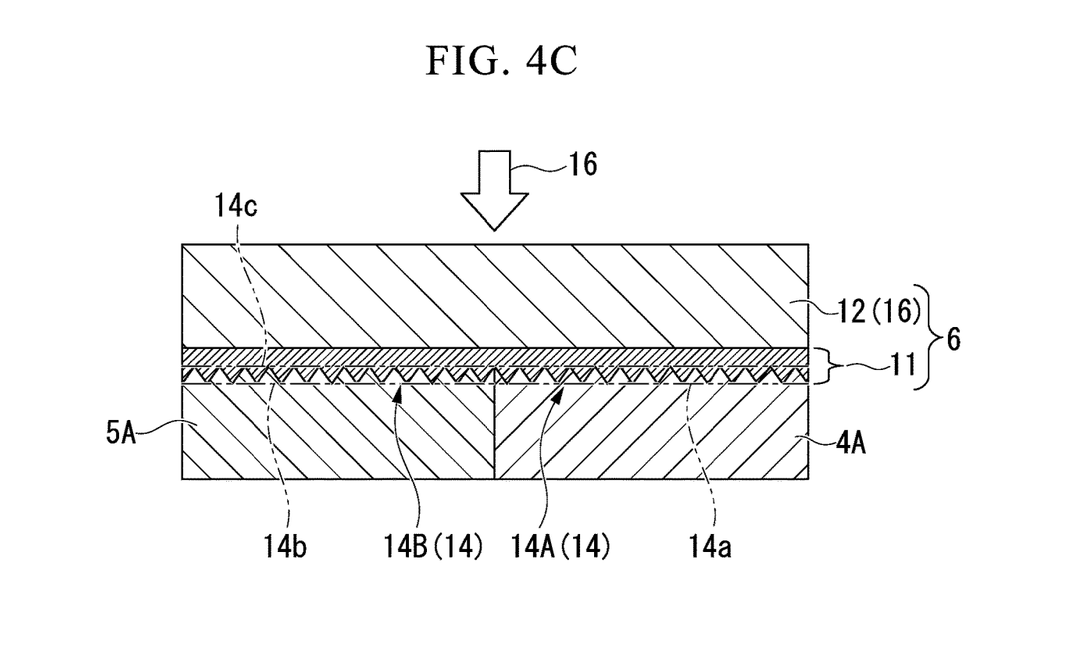
FIG. 4C is a process chart schematically showing the method for manufacturing a medical device.

FIG. 4A to FIG. 4C are process charts schematically showing the method for manufacturing the medical device according to an embodiment of the present disclosure.

At first, the external skin 4A and the external skin 5A are prepared. In particular, according to the present embodiment, the adhesion portion 6 is assembled in the state in which the external skin 4A and the external skin 5A cover the nodal rings and the corrugated tube, respectively. Further, the external skin 4A and the external skin 5A are in contact with each other.

In parallel with this, a underlayer solution for forming the underlayer 11 is prepared. The underlayer solution is prepared by mixing the isocyanate, a substance necessary to be contained in the underlayer 11, and an organic solvent.

The type of isocyanate is not particularly limited. As the isocyanate, for example, the diphenylmethane diisocyanate (MDI), the toluene diisocyanate (TDI), the hexamethylene diisocyanate (HDI) and the like may be used.

Examples of more preferable isocyanates that have unsaturated bonds between carbon atoms include the 2-isocyanatoethylacryllate, the 2-isocyanatoethyl methacrylate, the methacrylic acid 2-(0-[1'-methylpropyridaneamino) carboxyamino) ethyl, 2-[(3,5-dimethylpyrazolyl) carbonylamino] ethyl methacrylate, 1,1-(bisacryloyloxymethyl) ethyl isocyanate, and 2-isocyanatoethylacrylate.

The organic solvent only has to be able to dissolve the isocyanate forming the underlayer 11, and the type of the organic solvent is not particularly limited. However, if an organic solvent having a small surface energy is used as the organic solvent for the underlayer solution, it may be easy to coat on resin base. For example, as the organic solvent, the acetone, the methyl ethyl ketone, the toluene, the ethyl acetate, the tetrahydrofuran and the like may be used. Since the organic solvent shown above has a low surface energy than the water, it is suitable for coating the resin base containing fluorine.

The underlayer solution is coated to the surface of the resin base. The method of coating the underlayer solution is not particularly limited.

For example, the underlayer solution may be coated on the surface of the resin base. As a method of coating the underlayer solution, for example, the dipping, the brush coating, the spray coating or the like may be used.

For example, the underlayer solution may be coated on the resin base by immersing the resin base in the underlayer solution.

In the example shown in FIG. 4A, the underlayer solution 15 is coated on the surface 4a of the external skin 4A and the surface 5a of the external skin 5A by the dipping. The coating thickness of the underlayer solution 15 is appropriately set according to the target thickness of the underlayer 11.

When the underlayer solution 15 coated on the surface 4a and the surface 5a, the interaction between the underlayer solution 15 and the external skin 4A and the external skin 5A starts.

The isocyanate in the underlayer solution 15 is chemically active. The isocyanate attacks the chemical structure in the external skin 4A and the external skin 5A that can react with the isocyanate, and a chemical bond with the external skin 4A and the external skin 5A is formed.

In particular, when the underlayer solution 15 contains the substance having the unsaturated bond between carbon atoms, the substance having the unsaturated bond between carbon atoms chemically bonds with the components of the external skin 4A and the external skin 5A through the chemical reaction with the isocyanate.

As shown in FIG. 4B, when the interaction between the underlayer solution 15 and the external skin 4A and the external skin 5A proceeds, the surface 4a and the surface 5a are eroded, or the reactants are added to the surface 4a and the surface 5a such that fine uneven structure S4 and uneven structure S5 are formed respectively. As a result, the first composite layer 14A in which the first base material and the base material are composited is formed in the thickness range of the uneven structure S4, and the second composite layer 14B in which the second base material and the base material are composited is formed in the thickness range of the uneven structure S5.

On the other hand, the underlayer solution 15 at the portion apart from the external skin 4A and external skin 5A is solidified as the drying progresses or the heating progresses when heating is performed such that the underlayer main body 13 containing the isocyanate is formed on the composite layer 14.

The thickness of the composite layer 14 may be adjusted by controlling the progress of the interaction between the underlayer solution 15 and the external skin 4A and external skin 5A. For example, the thickness of the composite layer 14 may be adjusted by setting the adhesion time, the drying time, the drying temperature and the like of the underlayer solution 15 to the external skin 4A and external skin 5A until the underlayer solution 15 is dried.

The composite layer 14 and the underlayer main body 13 are laminated in this order on the external skin 4A and external skin 5A. At this time, since the composite layer 14 contains the chemical bond with the external skin 4A and external skin 5A, the composite layer 14 is firmly bonded with the external skin 4A and external skin 5A. As a result, even if the fluorine groups are exposed on the surface 4a and the surface 5a before the formation of the underlayer 11, the fluorine groups are covered by the underlayer 11.

Thereafter, as shown in FIG. 4C, a liquid epoxy resin raw material 16 is coated on the underlayer 11. For example, the epoxy resin raw material 16 is prepared as a mixture containing an epoxy resin and a curing agent.

The method for coating the epoxy resin raw material 16 is not particularly limited. For example, the epoxy resin raw material 16 may be coated by brush coating or the like.

Since the fluorine groups are not exposed on the underlayer 11, the epoxy resin raw material 16 is easily coated. After coating the epoxy resin raw material 16, the epoxy resin raw material 16 is cured by heating as necessary.

When the curing of the epoxy resin raw material 16 is completed, the epoxy resin layer 12 is formed.

During the curing process, the epoxy resin raw material 16 in contact with the underlayer 11 is firmly bonded to the underlayer 11 by chemically bonding with the isocyanate in the underlayer 11. As a result, the underlayer 11 contains an oxazolidone ring due to the chemical reaction between the isocyanate and the epoxy resin raw material 16.

In particular, when the underlayer 11 contains the substance having the unsaturated bond between carbon atoms, the substance having the unsaturated bond between carbon atoms chemically bonds with the epoxy resin raw material 16 via the chemical reaction with the isocyanate. As a result, the epoxy resin layer 12 is further firmly bonded to the underlayer 11.

According to the endoscope 1 according to the present embodiment, an adhesion portion 6 on which the epoxy resin layer 12 is arranged with the underlayer 11 sandwiched on the surface of the external skin 4A and external skin 5A formed from the resin containing the fluorine is formed.

Since the epoxy resin layer 12 is cured in close contact with the surface of the underlayer 11 on which the fluorine groups are not exposed, the epoxy resin layer 12 is firmly adhered to the underlayer 11.

Further, the chemical bond due to the isocyanate contained in the base material is formed between the external skin 4A, the external skin 5A and the underlayer 11, and between the underlayer 11 and the epoxy resin layer 12. As a result, the bonding force between the external skin 4A, the external skin 5A and the underlayer 11, and between the underlayer 11 and the epoxy resin layer 12 is improved.

In particular, according to the present embodiment, the external skin 4A, the external skin 5A and the underlayer 11 are joined with the composite layer 14 sandwiched therebetween. As a result, the bonding force between the external skin 4A, the external skin 5A and the underlayer 11 is improved in that the first base material, the second base material, and the base material are composited in a three-dimensional uneven structure.

According to the endoscope 1 according to the present embodiment, since the bonding force of the adhesion portion 6 can be improved, the durability of the adhesive portion using the resin base containing the fluorine as an adherend body may be improved.

[First Modification]

A medical device according to a first modification of the present embodiment will be described.

Figure 5:
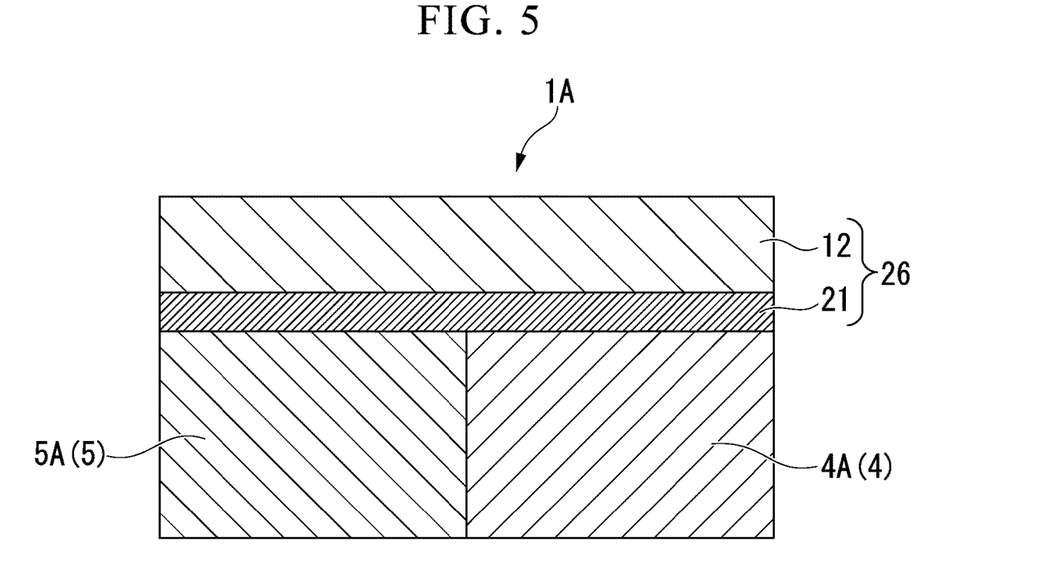
FIG. 5 is a cross-sectional view schematically showing an adhesion portion in a medical device according to a first modification of the above-described embodiment.

FIG. 5 is a schematic cross-sectional view showing an adhesive portion in a medical device according to the first modification of the embodiment of the present disclosure. The cross section shown in FIG. 5 corresponds to the A-A cross section shown in FIG. 2.

As shown in FIG. 1 and FIG. 2, the endoscope 1A according to the present modification is configured to include an adhesion portion 26 instead of the adhesion portion 6 of the endoscope 1 according to the present embodiment.

As schematically shown in FIG. 5, the adhesion portion 26 includes an underlayer 21 instead of the underlayer 11 of the adhesion portion 6 according to the embodiment.

Hereinafter, the points different from the above-described embodiment will be mainly described.

The underlayer 21 is configured in the same manner as the adhesion portion 6 according to the above-described embodiment except that the composite layer 14 is not formed. In other words, the underlayer 21 is a layered portion formed from the same base material as in the underlayer main body 13 according to the embodiment.

The adhesion portion 26 may be manufactured by adjusting the coating conditions of the underlayer solution 15. Specifically, the contact time between the underlayer solution 15 before drying and the external skin 4A, external skin 5A according to the present modification is set to be a length such that the isocyanate in the underlayer solution 15 can form a chemical bond with the external skin 4A and external skin 5A, and the underlayer solution 15 does not erode the external skin 4A and external skin 5A.

According to the endoscope 1A according to the present modification, since the composite layer is not formed, the chemical bond between the composite layer 14 and the external skin 4A, the external skin 5A as in the above-described embodiment is not formed; however, the bonding force due to the chemical bond due to the isocyanate is at the same degree as in the adhesion portion 6. Accordingly, according to the adhesion portion 26 according to the present modification, similar to the above-described embodiment, a higher bonding force may be obtained as compared with the case in which the epoxy resin layer 12 is directly formed on the external skin 4A and the external skin 5A such that it is possible to improve the durability of the adhesion portion using the resin base containing the fluorine as the adherend body.

[Second Modification]

Next, a medical device according to a second modification of the present embodiment will be described.

Figure 6:
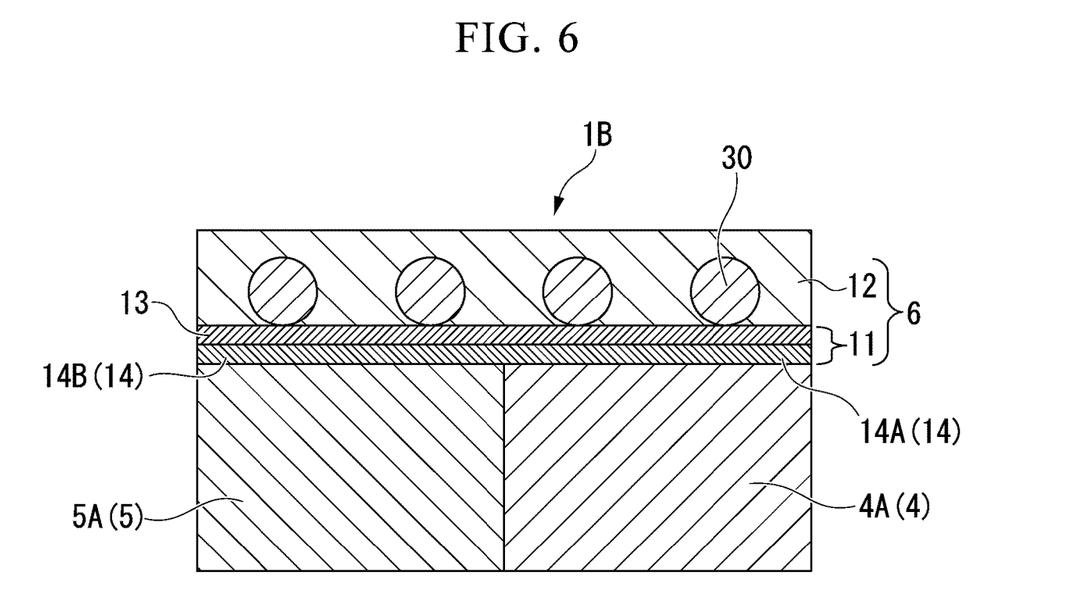
FIG. 6 is a cross-sectional view schematically showing an adhesion portion in a medical device according to a second modification of the above-described embodiment.

FIG. 6 is a schematic cross-sectional view of an adhesion portion in the medical device according to the second modification of the embodiment of the present disclosure. The cross section shown in FIG. 6 corresponds to the A-A cross section shown in FIG. 2.

As shown in FIG. 1 and FIG. 2, an endoscope 1B according to the present modification includes an adhesion portion 6 in the same manner of the endoscope 1 according to the embodiment. However, as schematically shown in FIG. 6, in this modification, a binding thread 30 is arranged on the outer circumferential portion of the underlayer 11.

Hereinafter, the points different from the embodiments will be mainly described.

According to the present modification, the binding thread 30 is wound around the outer circumferential portion of the underlayer 11 for the purpose of fixing the external skin 4A and the external skin 5A to a tubular mouthpiece (not shown) arranged inside the external skin 4A and the external skin 5A.

The material of the binding thread 30 is not particularly limited. For example, the nylon, the polyethylene terephthalate (PET), the silk or the like may be used as the material of the binding thread 30.

The epoxy resin layer 12 according to the present modification is formed after the underlayer 11 is formed on the outer circumferential portions of the external skin 4A and the external skin 5A and the binding thread 30 is wound around the underlayer 11. Accordingly, the adhesion portion 6 according to the present modification includes the binding thread 30 inside the epoxy resin layer 12.

According to the endoscope 1B according to the present modification, an uneven shape on the outer circumferential portions of the external skin 4A and external skin 5A is formed by the binding thread 30. The epoxy resin layer 12 of the adhesion portion 6 is formed on the underlayer 11 with the binding thread 30 covered. Even if an external force is applied on the epoxy resin layer 12, the epoxy resin layer 12 is bonded more firmly than the case in which the epoxy resin layer 12 is bonded to the smooth surface of the external skin 4A and the external skin 5A.

Therefore, according to the endoscope 1B of the present modification, it is possible to improve the durability of the adhesive portion using the resin base containing the fluorine as the adherend body.

According to the description of the above-described embodiment and each modification, the case where the medical device is the endoscope has been described as an example. However, the medical device which may be used as the medical device according to the present disclosure is not limited to the endoscope. The medical device according to the present disclosure may be adopted from medical devise such as the treatment tools, the syringes, the cleaning devices, therapeutic devices or the like.

According to the description of the above-described embodiment and each modification, the case where the resin base is the tubular external skin 4A and the external skin 5A has been described as an example. However, the resin base is not limited to the tubular shape. For example, the resin base may have a shape such as the plate shape, the sheet shape, the rod shape, the lump shape or the like.

The resin base may be used for any member as long as it is a member of a medical device.

According to the description of the above-described embodiment and each modification, the case where two resin bases containing the fluorine are arranged adjacent to each other, and each resin base is covered with the underlayer and the epoxy resin layer is described as an example.

However, the two resin substrates may be opposite to each other in the layer thickness direction. In this case, the underlayer is formed on the surface of each resin base, and the epoxy resin layer is formed between the underlayers.

Further, the appropriate adherend body formed from a material that can be bonded by the epoxy resin layer may be arranged on the epoxy resin layer. In this case, the adherend body is bonded to the resin base containing the fluorine via the underlayer and the epoxy resin layer.

According to the description of the above-described embodiment and each modification, an example in which the composite layer is formed when the underlayer solution and the resin base come into contact with each other has been described. However, the underlayer may be formed by coating the second underlayer solution formed from the raw material of the underlayer main body on the composite layer after coating the first underlayer solution in which the raw material of the resin base and the raw material of the underlayer main body are composited thereon.

EXAMPLES

Next, examples of the medical device according to the above-described embodiment and the first modification will be described together with a comparative example.

The following [Table 1] shows the configurations and evaluation results of the Examples 1 to 6 and the Comparative Example 1. In [Table 1], the reference numerals designated to the member names are omitted.

TABLE 1

| | UNDER-LAYER | THICKNESS OF COMPOSITE LAYER (nm) | CROSS-CUT TEST CLASSI-FICATION | JUDGE-MENT |
|---|---|---|---|---|
| EXAMPLE 1 | YES | — | 2 | OK |
| EXAMPLE 2 | YES | 2 | 1 | OK |
| EXAMPLE 3 | YES | 300 | 1 | OK |
| EXAMPLE 4 | YES | 100 | 0 | OK |
| EXAMPLE 5 | YES | 100 | 0 | OK |
| EXAMPLE 6 | YES | 4 | 1 | OK |
| COMPARISON EXAMPLE 1 | NO | — | 3 | NG |

Example 1

The Example 1 is an example corresponding to the first modification. In Example 1, an endoscope tube (hereinafter referred to as a tube) as the resin base used as the evaluation sample and formed from the ethylene propylene resin containing the fluorine was prepared. As the fluorine-containing ethylene propylene resin, the tetrafluoroethylene/hexafluoropropylene copolymer resin was used.

The shape of the tube was formed to be 2 mm in thickness, 15 mm in outer diameter, and 2000 mm in length. The resin base was commonly used in each of Examples and the Comparative Example 1 described later.

The underlayer 21 of Example 1 was formed as follows using a underlayer solution 15 in which MDI was dissolved in 1% by mass with an acetone solvent.

The end of the tube was immersed in the underlayer solution 15 for 3 seconds, and the underlayer solution 15 was adhered to the outer circumference of the tube in a width of 100 mm over the entire circumference.

The tube was heated to 60 degrees Celsius for 30 minutes for the purpose of drying the substrate solution 15 and facilitating the interaction between the MDI and the tube. As a result, the underlayer 21 was formed on the outer circumferential surface of the tube.

For the purpose of forming the epoxy resin layer 12, a liquid epoxy resin raw material 16 formed from a mixture of a bisphenol A type epoxy resin and an aromatic amine-based curing agent was prepared.

An amount of the epoxy resin raw material 16 so as to have a thickness of 100 μm after being cured was coated onto the underlayer 21. The brush coating method was used as the coating method.

The tube after application was cured by being heated to 80 degrees Celsius for 2 hours.

The evaluation sample of Example 1 was manufactured following the above-mentioned steps.

When the composition of the underlayer 21 was analyzed by observing the cross section of the evaluation sample of Example 1, as shown in [Table 1], the composite layer was not formed or the composite layer was less than the measurement limit even if the composite layer was actually formed.

Example 2 and Example 3

Example 2 and Example 3 are examples corresponding to the embodiment.

The evaluation samples of Example 2 and Example 3 were produced in the same manner as that in Example 1 except that the immersion time of the tube in the underlayer solution 15 was set to 10 seconds and 20 seconds, respectively.

When the composition of the underlayer 11 was analyzed by observing the cross sections of the evaluation samples of Example 2 and Example 3, as shown in [Table 1], the thickness of the composite layer 14 was 2 nm and 300 nm, respectively.

Example 4

Example 4 is an example corresponding to the embodiment. In Example 4, a solution prepared by mixing 1.0 g of Calends AOI (registered trademark) (product name; manufactured by Showa Denko KK) with 9.0 g of methyl ethyl ketone (MEK) was used as the underlayer solution 15. The Calends AOI (registered trademark) was formed from the 2-isocyanatoethylacryllate. The material of the 2-Isocyanatoethylacryllate is an isocyanate containing one carbon-to-carbon double bond per molecule.

The underlayer 11 of Example 4 was formed in the same manner as that in Example 1 except that the end of the tube was immersed in the underlayer solution 15 for 15 seconds.

The epoxy resin layer 12 of Example 4 was formed in the same manner as that in Example 1.

When the composition of the underlayer 11 was analyzed by observing the cross section of the evaluation sample of Example 4, the thickness of the composite layer 14 was 100 nm, as shown in [Table 1].

Example 5

Example 5 is an example corresponding to the embodiment.

In Example 5, a solution prepared by mixing 1.0 g of Calends AOI (registered trademark) (product name; manufactured by Showa Denko KK) and 0.1 g of Perhexa (registered trademark) 25B (product name; manufactured by Nippon Oil & Chemicals Co., Ltd.) into 9.0 g of MEK was used as the underlayer solution 15. The material of Perhexa (registered trademark) 25B was a peroxide and was used as a reactive cross linker for the unsaturated carbon bonds.

The evaluation sample of Example 5 was produced in the same manner as in Example 4 except that 0.1 g of Perhexa (registered trademark) 25PE was added to the underlayer solution 15.

When the composition of the underlayer 11 was analyzed by observing the cross section of the evaluation sample of Example 5, the thickness of the composite layer 14 was 100 nm, as shown in [Table 1].

Example 6

Example 6 is an example corresponding to the embodiment.

In Example 6, the underlayer solution 15 was manufactured in the same manner as that in Example 2 except that the underlayer solution 15 in which TDI was dissolved in 1% by mass with an acetone solvent was used.

When the composition of the underlayer 11 was analyzed by observing the cross section of the evaluation sample of Example 6, the thickness of the composite layer 14 was 4 nm as shown in [Table 1].

Comparative Example 1

The evaluation sample of Comparative Example 1 was produced by forming the epoxy resin layer 12 in the same manner as that in Example 1 without forming the underlayer on the surface of the tube.

[Evaluation]

As shown in [Table 1], a cross-cut test was performed as an evaluation of each Example and Comparative Example 1.

The cross-cut test was performed on each evaluation sample immersed in a mixed solution of acetic acid/peracetic acid/hydrogen peroxide for 24 hours. The cross-cut test was performed in accordance with the JIS K5600-5-6 cross-cut method. The evaluation results were represented by classifications 0 to 5 according to the same JIS K5600-5-6. The classification number indicates that the adhesion characteristic is better if the value is smaller.

When the evaluation result was in the classification 0 to 2, it was judged that the adhesion between the tube and the epoxy resin layer was good (shown by "good" in [Table 1]). When the evaluation results were classified into classification 3 to 5, the adhesion between the tube and the epoxy resin layer was judged to be poor (indicated by "NG" in [Table 1]).

[Evaluation Results]

As shown in [Table 1], the results of the cross-cut test were indicated as follows: Example 1 was in classification 2, Example 2, Example 3 and Example 6 were in classification 1, and Example 4 and Example 5 were in classification 0.

Accordingly, all of Examples 1 to 6 were judged to have good adhesion characteristic.

On the other hand, the judgment of the cross-cut test in Comparative Example 1 was in classification 3 such that the adhesion characteristic was judged to be poor.

As described above, in Examples 1 to 6, it is considered that the adhesion between the fluorine-containing resin base and the epoxy resin layer was improved as a result of the formation of the underlayer. On the other hand, in Comparative Example 1, it is considered that the adhesion between the fluorine-containing resin base and the epoxy resin layer was poor since the underlayer is not formed.

In Examples 4 and 5, since the substance having the unsaturated bond between carbon atoms was contained in the underlayer 11, this substance and the resin base or the epoxy resin were chemically bonded with the isocyanate such that it is considered that the adhesion characteristic is improved.

Although the embodiment and each modification of the present disclosure have been described above together with each example, the present disclosure is not limited to these embodiments, modifications, and examples. Configurations may be added, omitted, replaced, and other modifications without departing from the spirit of the present disclosure may be realized.

Further, the present disclosure is not limited by the above description and is limited only by the appended claims.

What is claimed is:

1. A medical device, comprising:
   a resin base including one or more than one material selected from the group consisting of an ethylene propylene resin containing fluorine, a styrene resin containing fluorine, an olefin resin containing fluorine, a vinyl chloride resin containing fluorine, a polyester resin containing fluorine, a polyurethane resin containing fluorine, and a nylon resin containing fluorine;
an underlayer formed on the resin base, the underlayer including an oxazolidone ring; and
an epoxy resin layer formed on the underlayer,
wherein at least one of the resin base and the underlayer comprises a substance having an unsaturated bond of carbon atoms, and the resin base and the underlayer are composited in a three-dimensional uneven structure.

2. The medical device according to claim 1, wherein a composite layer including the material of the resin base is formed at least in a lower portion of the underlayer.

3. The medical device according to claim 2, wherein a thickness of the composite layer is equal to or more than 2 nanometers and equal to or less than 800 nanometers.

4. The medical device according to claim 1, wherein:
the medical device is an endoscope comprising an insertion portion and an operating portion;
the insertion portion comprises a flexible tube portion, a bending portion, and a distal end portion;
the bending portion is connected to a proximal end side of the distal end portion, and the bending portion is configured to change an orientation of the distal end portion;
the flexible tube portion connects the operation portion and the bending portion;
the flexible tube portion has a first external skin comprising the resin base;
the bending portion has a second external skin comprising the resin base;
an adhesion portion is provided at a position where the first and second external skins are adjacent to each other, and covers an external circumference of the first external skin and an external circumference of the second external skin;
the adhesion portion comprises the underlayer and the epoxy resin; and
underlayer of the adhesion portion is formed on the resin base of the first external skin and the resin base of the second external skin.

5. The medical device according to claim 1, wherein the resin base contains, as the substance having the unsaturated bond of carbon atoms, an acrylic resin containing fluorine, a vinyl ester resin containing fluorine, a vinyl acetate resin containing fluorine, or a vinylidene resin containing fluorine.

6. The medical device according to claim 1, wherein the underlayer contains as the substance having the unsaturated bond of carbon atoms, 2-isocyanatoethylacrylate or 2-isocyanatoethyl methacrylate.

7. The medical device according to claim 1, wherein the underlayer contains as the substance having the unsaturated bond of carbon atoms, 2-isocyanatoethylacrylate, 2-isocyanatoethyl methacrylate, methacrylic acid, 2-(0-[1'-methylpropyridaneamino] carboxyamino) ethyl, 2-[(3,5-dimethylpyrazolyl) carbonylamino] ethyl methacrylate, 1,1-(bisacryloyloxymethyl) ethyl isocyanate, or 2-isocyanatoethylacrylate.

8. A method for manufacturing the medical device of claim 1, the method comprising:
preparing the resin base including one or more than one material selected from the group consisting of an ethylene propylene resin containing fluorine, a styrene resin containing fluorine, an olefin resin containing fluorine, a vinyl chloride resin containing fluorine, a polyester resin containing fluorine, a polyurethane resin containing fluorine, and a nylon resin containing fluorine;
preparing a solution in which isocyanate is mixed in an organic solvent;
adhering the solution on a surface of the resin base material and drying the solution to form the underlayer; and
coating an epoxy resin raw material on the underlayer and curing the epoxy resin raw material to form the epoxy resin layer.

9. The method according to claim 8, further comprising forming a composite layer in a lower portion of the underlayer, wherein the material of the underlayer and the material of the resin base are mixed in the composite layer.

* * * * *